United States Patent
Lee

(10) Patent No.: US 6,223,376 B1
(45) Date of Patent: May 1, 2001

(54) TOOTHBRUSH FOR BABIES

(76) Inventor: Joong Woo Lee, Jukong Apt. 1210-1201, Ilaon-Dong, Kwangmyong-Shi, Kyonggi-Do (KR)

(*) Notice: Subject to any disclaimer, the term of this patent is extended or adjusted under 35 U.S.C. 154(b) by 0 days.

(21) Appl. No.: 09/592,329

(22) Filed: Jun. 13, 2000

(51) Int. Cl.⁷ .................................................... A46B 13/00
(52) U.S. Cl. ............................................................. 15/22.1
(58) Field of Search .............................. 15/22.1; 606/234, 606/235, 236

(56) References Cited

U.S. PATENT DOCUMENTS

| | | | |
|---|---|---|---|
| 4,011,616 | * | 3/1977 | Kennedy . |
| 4,224,710 | * | 9/1980 | Solow . |
| 4,237,574 | * | 12/1980 | Kelly . |
| 5,175,901 | * | 1/1993 | Rabinowitz . |
| 5,337,435 | * | 8/1994 | Krasner . |
| 5,365,624 | * | 11/1994 | Berns . |

* cited by examiner

Primary Examiner—Randall E. Chin
(74) Attorney, Agent, or Firm—Colin P. Abrahams

(57) ABSTRACT

Disclosed is a toothbrush. The toothbrush comprises a toothbrush body having a handle and a first vibration generating section and possessing a first groove which has substantially a U-shaped contour; an intermediate engaging member detachably engaged into the first groove of the toothbrush body, having substantially a U-shaped configuration, and possessing a second groove which has substantially a U-shaped contour; a bristle holder having anchored thereto a plurality of bristles, the bristle holder including a teeth cleaning section and a tongue cleaning section; the teeth cleaning section being detachably fitted into the second groove of the intermediate engaging member, having substantially a U-shaped configuration, and possessing a third groove which has substantially a U-shaped contour to receive therein upper or lower teeth of a person; and the tongue cleaning section integrally coupled to a curved portion of the teeth cleaning section for removing a coating existing on a surface of the tongue of the person.

5 Claims, 4 Drawing Sheets

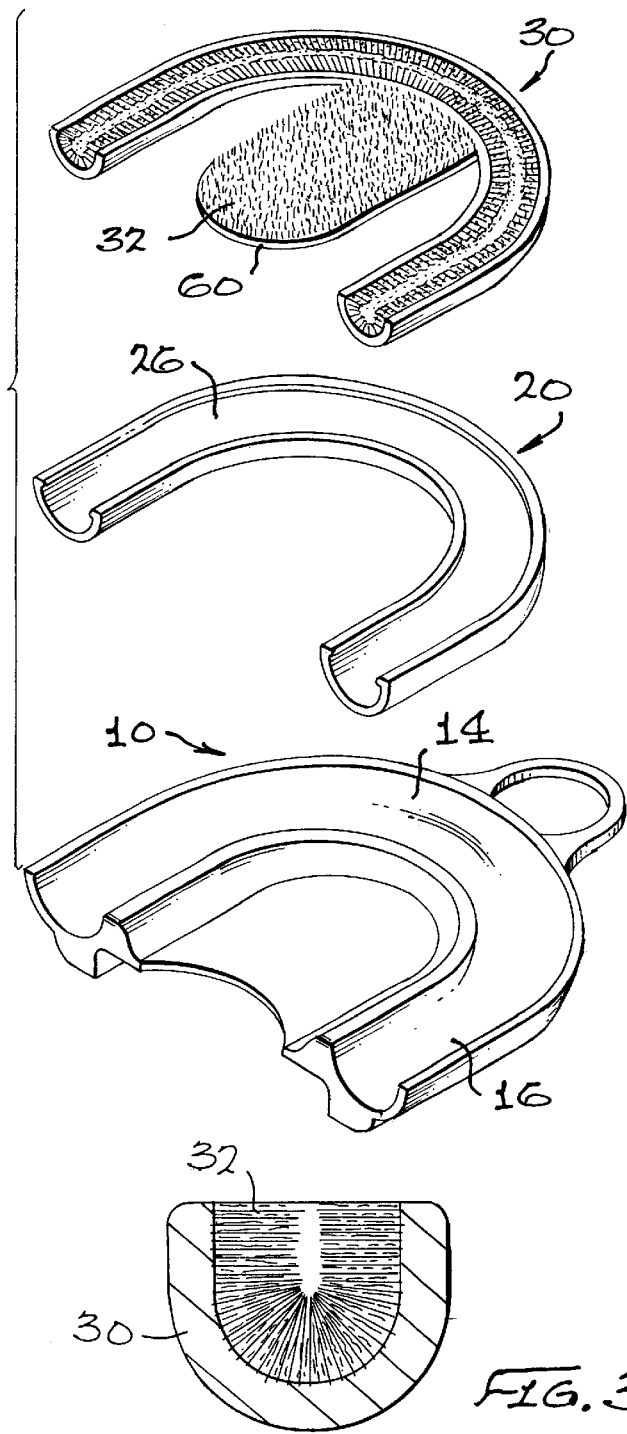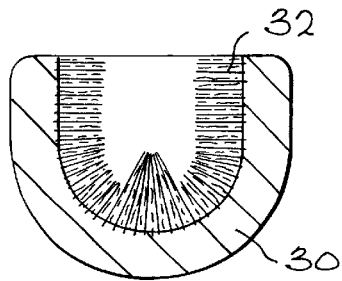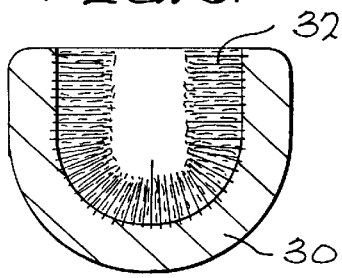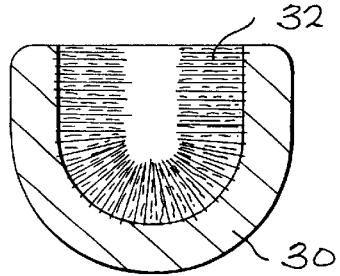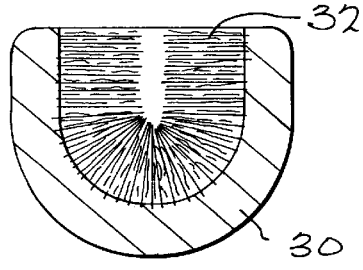

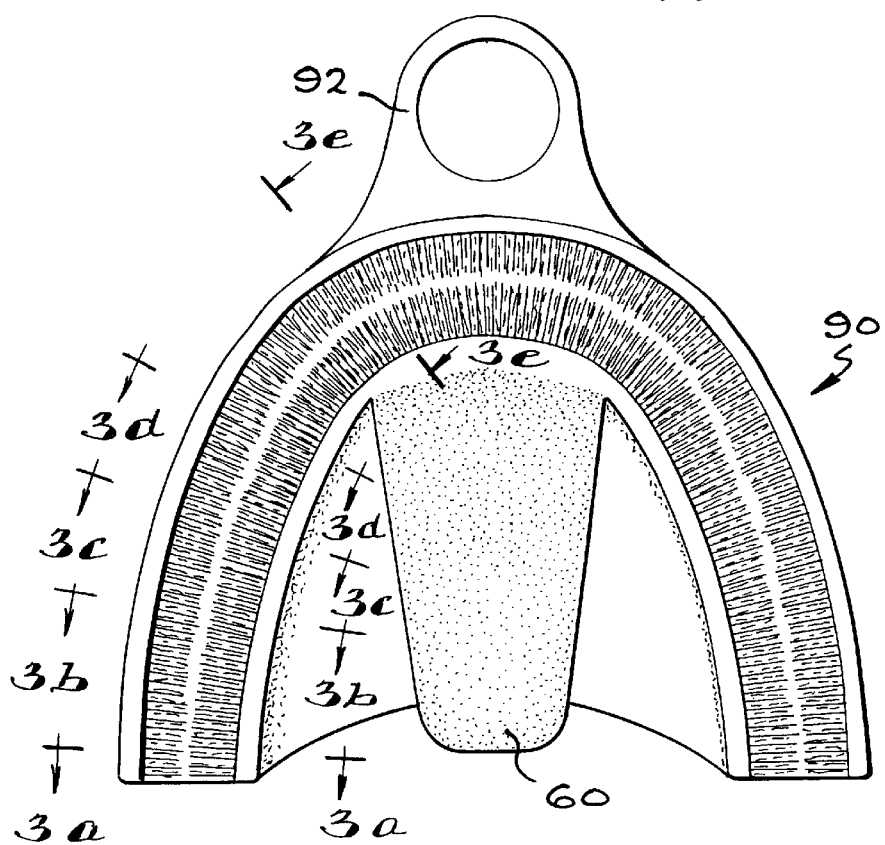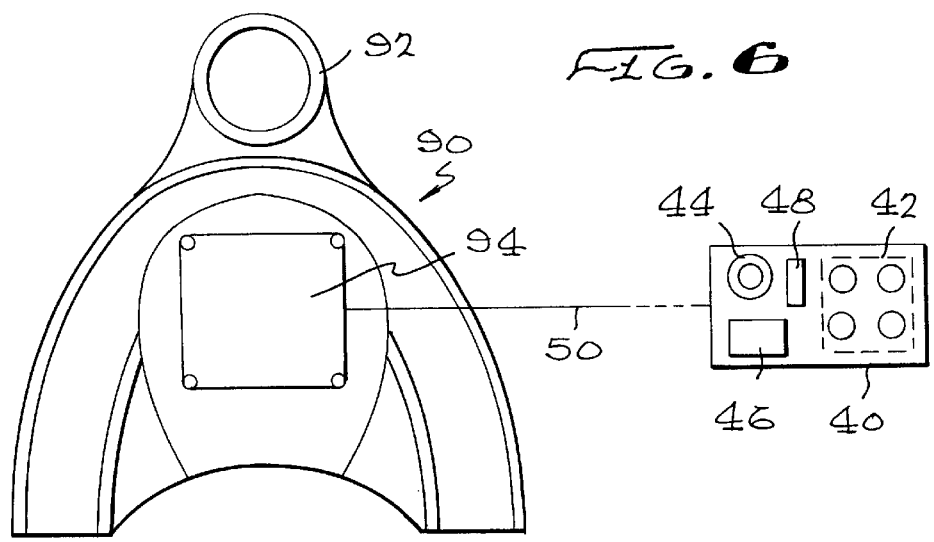

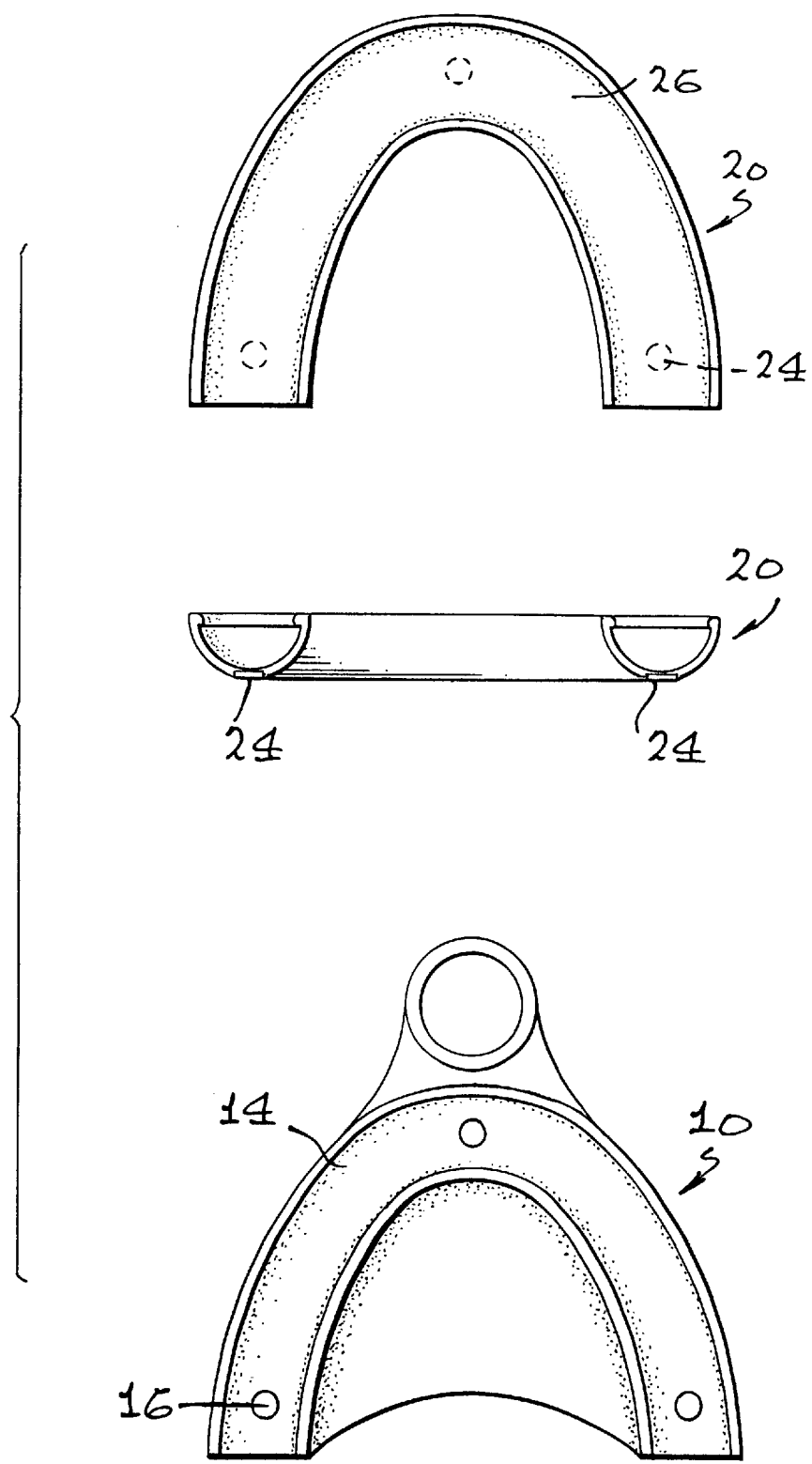

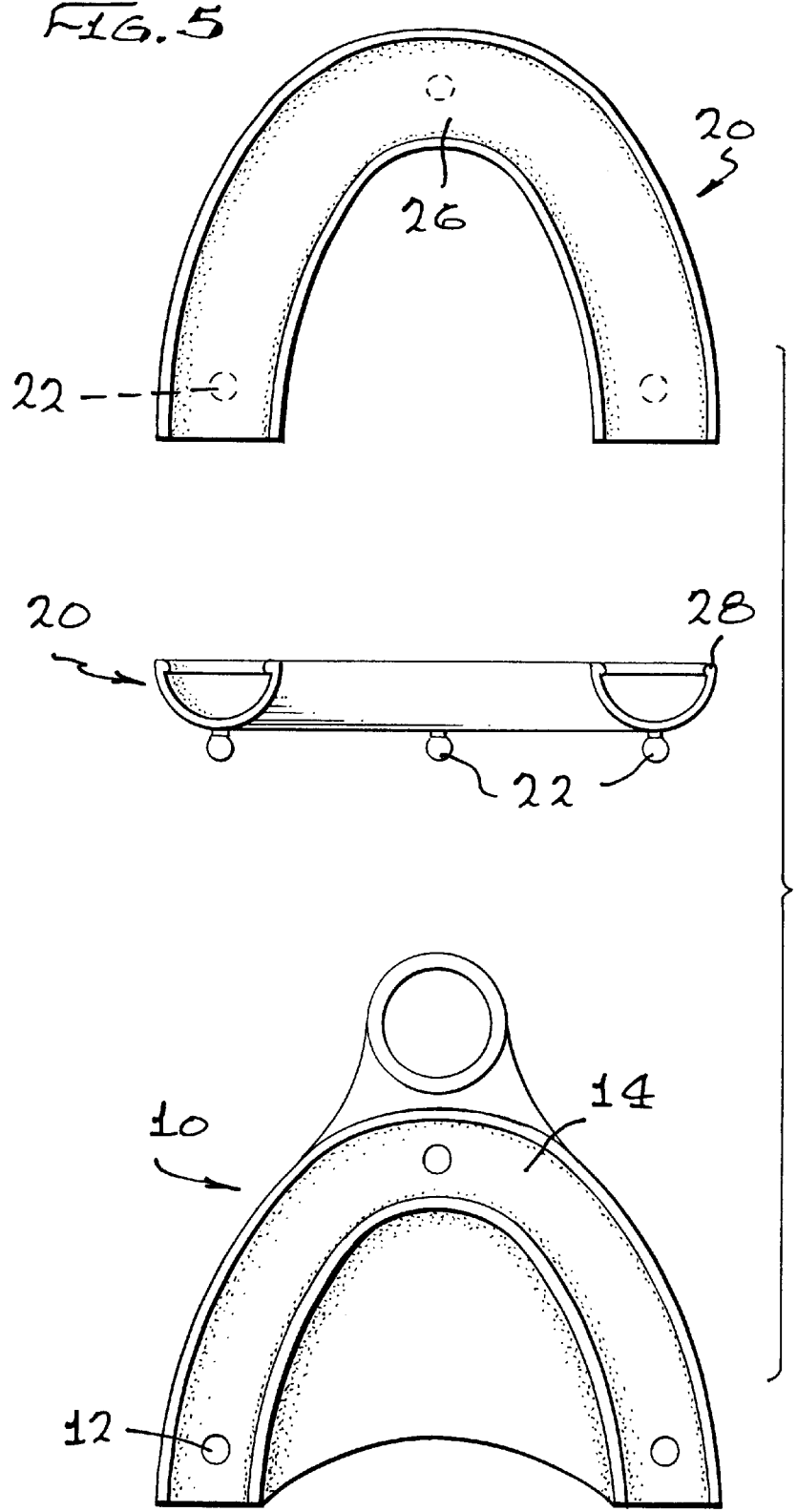

TOOTHBRUSH FOR BABIES

BACKGROUND OF THE INVENTION

1. Field of the Invention

The present invention relates to a toothbrush for babies, and ore particularly, the present invention relates to a toothbrush for babies which can be received in the mouth of a baby, for example, aged not more than 5 years and can simultaneously and thereby rapidly clean all of upper teeth or all of lower teeth of the baby.

2. Description of the Related Art

Generally, a tooth of a baby starts to erupt from 6 months to 12 months since birth, and a deciduous dentition is completed at 24 months to 36 months since birth. In this way, after the deciduous dentition of a baby is completed within 36 months since birth, all deciduous (milk) teeth are replaced with permanent teeth before the baby is 11-years old. At this time, if the deciduous teeth which are to be replaced with the permanent teeth, are not carefully administrated, the permanent teeth cannot be properly formed and malocclusion is caused, whereby facial features may be distorted or bothersomeness or inconvenience may be provoked in administrating the permanent teeth. Consequently, in order to administrate the deciduous teeth of a baby in an adequate manner, a parent must frequently brush the teeth of the baby. However, when a parent brushes the teeth of a baby using a toothbrush or another implement, since toothbrushing is considered as an unpleasant, if not painful, drudging by the baby, the baby develops a hatred for the toothbrushing. Hence, it is difficult for the parent to sufficiently brush the teeth of the baby. Stated otherwise, in the case that the parent brushes teeth of a baby using the conventional toothbrush, a toothbrushing operation cannot be correctly implemented by the parent. Furthermore, as a substantial time is lapsed in implementing the toothbrushing operation, because the baby can show severe reluctancy thereto, the likelihood of dental plague not to be properly removed is increased.

SUMMARY OF THE INVENTION

Accordingly, the present invention has been made in an effort to solve the problems occurring in the related art, and an object of the present invention is to provide a toothbrush for babies which can simultaneously clean all of upper teeth or all of lower teeth of a baby.

Another object of the present invention is to provide a toothbrush for babies which can not only clean teeth, but also remove a coating existing on a surface of the tongue of a baby.

According to one aspect of the present invention, there is provided a toothbrush comprising: a toothbrush body having a handle and a first vibration generating section and possessing a first groove which has substantially a U-shaped contour; an intermediate engaging member detachably engaged into the first groove of the toothbrush body, having substantially a U-shaped configuration, and possessing a second groove which has substantially a U-shaped contour; a bristle holder having anchored thereto a plurality of bristles, the bristle holder including a teeth cleaning section and a tongue cleaning section; the teeth cleaning section being detachably fitted into the second groove of the intermediate engaging member, having substantially a U-shaped configuration, and possessing a third groove which has substantially a U-shaped contour to receive therein upper or lower teeth of a person; and the tongue cleaning section integrally coupled to a curved portion of the teeth cleaning section for removing a coating existing on a surface of the tongue of the person.

According to another aspect of the present invention, the toothbrush further comprises a remote controller including at least one switch for controlling an operation of the first vibration generating section, a speaker for outputting music, a light emitting section capable of flickering, and a second vibration generating section for exerting vibration to an operator's hand, the remote controller being connected to the first vibration generating section of the toothbrush body through a wire.

According to another aspect of the present invention, each of the first through third grooves of the toothbrush body, the intermediate engaging member and the teeth cleaning section of the bristle holder, respectively, has substantially the U-shaped contour in a manner such that it conforms to an outline of gums of the person.

According to still another aspect of the present invention, the bristle holder and the plurality of bristles are made from silicon.

According to yet still another aspect of the present invention, the bristles which are anchored at one ends thereof to a surface of the teeth cleaning section of the bristle holder, define a variety of different figures in a manner such that they can simultaneously clean buccal, lingual and occlusal surfaces of posterior teeth and labial and lingual surfaces of anterior teeth of the person.

By the features of the present invention, advantages are provided in that, since first through third grooves of a toothbrush body, an intermediate engaging member and a teeth cleaning section of a bristle holder have substantially U-shaped contours, respectively, all of upper teeth or all of lower teeth which are formed in gums of a baby, can be simultaneously cleaned. Also, due to the fact that the bristle holder and a plurality of bristles are made from a soft material such as silicon, awkwardness or uncomfortableness is not induced when they are brought into contact with the teeth and gums of the baby. At this time, the plurality of bristles which are anchored at one ends thereof to a surface of the teeth cleaning section of the bristle holder, define different profiles at posterior teeth and anterior teeth of the baby, in a manner such that they can simultaneously clean buccal, lingual and occlusal surfaces of the posterior teeth and labial and lingual surfaces of the anterior teeth. As a consequence, after the toothbrush of the present invention is received in the mouth of the baby, in a state wherein the plurality of bristles are brought into contact with the teeth and gums of the baby, vibration is generated using a first vibration generating section, whereby, as the toothbrush is continuously moved little at a time in forward, rearward, leftward or rightward directions, all of upper teeth or all of lower teeth can be simultaneously cleaned.

BRIEF DESCRIPTION OF THE DRAWINGS

The above objects, and other features and advantages of the present invention will become more apparent after a reading of the following detailed description when taken in conjunction with the drawings, in which:

FIG. 1 is an exploded perspective view of a toothbrush for babies in accordance with a first embodiment of the present invention;

FIG. 2 is a plan view schematically illustrating a state wherein the toothbrush for babies according to the present invention is assembled;

FIG. 3a is a cross-sectional view taken along the line 3a—3a of FIG. 2;

FIG. 3b is a cross-sectional view taken along the line 3b—3b of FIG. 2;

FIG. 3c is a cross-sectional view taken along the line 3c—3c of FIG. 2;

FIG. 3d is a cross-sectional view taken along the line 3d—3d of FIG. 2;

FIG. 3e is a cross-sectional view taken along the line 3e—3e of FIG. 2;

FIG. 4 is of a plan view of a toothbrush body and front and bottom views of an intermediate engaging member, with the toothbrush body and the intermediate engaging member constituting the toothbrush according to the first embodiment of the present invention;

FIG. 5 is of a plan view of a toothbrush body and front and bottom views of an intermediate engaging member, with the toothbrush body and the intermediate engaging member constituting the toothbrush according to a second embodiment of the present invention; and FIG. 6 is a bottom view schematically illustrating a remote controller which is connected to the toothbrush according to the present invention.

DETAILED DESCRIPTION OF PREFERRED EMBODIMENTS

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is an exploded perspective view of a toothbrush for babies in accordance with a first embodiment of the present invention; FIG. 2 is a plan view schematically illustrating a state wherein the toothbrush for babies according to the present invention is assembled; FIG. 3a is a cross-sectional view taken along the line 3a—3a of FIG. 2; FIG. 3b is a cross-sectional view taken along the line 3b—3b of FIG. 2; FIG. 3c is a cross-sectional view taken along the line 3c—3c of FIG. 2; FIG. 3d is a cross-sectional view taken along the line 3d—3d of FIG. 2; FIG. 3e is a cross-sectional view taken along the line 3e—3e of FIG. 2; FIG. 4 is of a plan view of a toothbrush body and front and bottom views of an intermediate engaging member, with the toothbrush body and the intermediate engaging member constituting the toothbrush according to the first embodiment of the present invention; FIG. 5 is of a plan view of a toothbrush body and front and bottom views of an intermediate engaging member, with the toothbrush body and the intermediate engaging member constituting the toothbrush according to a second embodiment of the present invention; and FIG. 6 is a bottom view schematically illustrating a remote controller which is connected to the toothbrush according to the present invention.

Referring to FIGS. 1 through 6, a toothbrush 90 for babies, according to the present invention, includes a toothbrush body 10. The toothbrush body 10 has a handle 92 and a first vibration generating section 94. A remote controller 40 which includes a plurality of switches 42 for controlling an operation of the first vibration generating section 94, a speaker 44 for outputting music and a second vibration generating section 46, is connected to the first vibration generating section 94 of the toothbrush body 10 through a wire 50. The toothbrush 90 further includes an intermediate engaging member 20 and a bristle holder 30. The bristle holder 30 has a teeth cleaning section (not separately numbered) and a tongue cleaning section 60.

Each of the toothbrush body 10, the intermediate engaging member 20 and the teeth cleaning section of the bristle holder 30 has substantially a U-shaped configuration which conforms to an arrangement of teeth and gums of a baby, in such a manner that a plurality of bristles 32 of the toothbrush 90 can be simultaneously brought into contact with all upper teeth or all lower teeth of the baby when the toothbrush 90 is used, thereby to clean them.

The first vibration generating section 94 is installed on a lower surface of the toothbrush body 10 which constitutes the toothbrush 90, and a first groove 14 is defined on an upper surface and along an edge portion of the toothbrush body 10. The first groove 14 has substantially a U-shaped contour. Three first magnets 16 are attached to a bottom of the first groove 14 so that they are spaced apart one from another along the first groove 14.

A second groove 26 is defined on an upper surface of the intermediate engaging member 20 and has substantially a U-shaped contour. Three second magnets 24 are attached to a lower surface of the intermediate engaging member 20 so that they are spaced apart one from another along a direction in which the intermediate engaging member 20 extends. The intermediate engaging member 20 is engaged into the first groove 14 which is defined in the toothbrush body 10. Due to the fact that the three first magnets 16 which are attached to the bottom of the first groove 14 of the toothbrush body 10 and the three second magnets 24 which are attached to the lower surface of the intermediate engaging member 20, are coupled with each other, respectively, the intermediate engaging member 20 is fastened to the toothbrush body 10 inside the first groove 14.

A third groove is defined on an upper surface of the teeth cleaning section of the bristle holder 30, and the tongue cleaning section 60 is integrally coupled to a curved portion of the teeth cleaning section. The third groove has substantially a U-shaped contour to receive therein upper teeth or lower teeth of the baby. The teeth cleaning section of the bristle holder 30 is detachably fitted into the second groove 26 of the intermediate engaging member 20. At this time, a pair of engaging projections 28 are formed along both edge portions, respectively, of the intermediate engaging member 20, in a manner such that the teeth cleaning section of the bristle holder 30 is fixedly maintained inside the second groove 26 of the intermediate engaging member 20. The bristle holder 30 is made from silicon and the intermediate engaging member 20 is made from a plastic material which has a predetermined flexibility.

The plurality of bristles 32 which are made from silicon, are anchored to upper surfaces of the teeth cleaning section and the tongue cleaning section 60 of the bristle holder 30. The bristles 32 which are anchored at one ends thereof to the upper surface of the teeth cleaning section of the bristle holder 30, define a variety of different figures depending upon shapes of the teeth. In other words, the bristles 32 which are to be brought into contact with a molar tooth, are anchored to the upper surface of the teeth cleaning section of the bristle holder 30 in a manner such that they define a wider inner space to receive therein the molar tooth. On the contrary, the bristles 32 which are to be brought into contact with a front tooth, are anchored to the upper surface of the teeth cleaning section of the bristle holder 30 in a manner such that they define a narrower inner space to receive therein the front tooth. As a consequence, the plurality of bristles 32 can simultaneously clean buccal, lingual and occlusal surfaces of posterior teeth and labial and lingual surfaces of anterior teeth of the baby.

Also, according to another embodiment of the present invention, by forming three locking protrusions 22 on the lower surface of the intermediate engaging member 20 at places where the three second magnets 24 are positioned and by defining three locking grooves 12 to the bottom of the first groove 14 of the toothbrush body 10 at places where the three first magnets 16 are positioned, due to the fact that the three locking protrusions 22 are locked into the three locking grooves 12, respectively, the intermediate engaging member 20 is fastened to the toothbrush body 10 inside the first groove 14.

Further, as described above, the third groove is defined on the upper surface of the teeth cleaning section of the bristle holder 30, and the tongue cleaning section 60 is integrally coupled to the curved portion of the teeth cleaning section. The third groove has substantially the U-shaped contour to receive therein the upper teeth or the lower teeth of the baby. The bristles 32 which are anchored to the upper surface of the tongue cleaning section 60, function to clean a surface of the tongue of the baby and thereby remove a coating existing thereon.

Hereinafter, operations of the toothbrush 90 for babies according to the present invention, constructed as mentioned above, will be described in detail.

After the bristle holder 30 to which the plurality of bristles 32 are anchored, is fitted into the second groove 26 of the intermediate engaging member 20 at the teeth cleaning section, by engaging the intermediate engaging member 20 into the first groove 14 of the toothbrush body 10, as the first magnets 16 which are disposed in the first groove 14 of the toothbrush body 10 and the second magnets 24 which are attached to the lower surface of the intermediate engaging member 20 are attracted by each other, the intermediate engaging member 20 is fastened to the toothbrush body 10. In a state wherein the toothbrush body 10, the intermediate engaging member 20 and the bristle holder 30 are fastened one to another, after the toothbrush 90 is received in the mouth of the baby and brought into contact with the upper teeth or the lower teeth of the baby, one of the switches 42 is turned on to actuate the first vibration generating section 94 which is provided on the remote controller 40. If the switch 42 is turned on, as the first vibration generating section 94 vibrates, the toothbrush body 10, the intermediate engaging member 20 and the bristle holder 30 also vibrate to enable the plurality of bristles 32 to clean the teeth of the baby. Also, as the bristle holder 30 massages and stimulates the gums of the baby with even pressure without causing injury thereto, it is possible to facilitate blood circulation in the gums thereby to strengthen the gums.

In addition, while an operator, for example, a parent, brushes the teeth of the baby using the toothbrush 90 according to the present invention, because it is possible to output music through the speaker 44 which is provided on the remote controller 40, the baby's attention can be auditorily turned to the music, whereby a degree of reluctancy of the baby to the toothbrushing can be lessened to a certain extent. Besides, in a state wherein the second vibration generating section 46 which is also provided on the remote controller 40, is turned on, if the baby who performs the toothbrushing operation by himself or herself touches the second vibration generating section 46 by the hand, it is possible to touchedly turn the baby's attention to the second vibration generating section 46, whereby a degree of reluctancy of the baby to the toothbrushing can be further lessened to a certain extent. Moreover, by causing a light emitting section 48 which is provided on the remote controller 40 as well, to flicker, it is possible to visually turn the baby's attention to the light emitting section 48, whereby a degree of reluctancy of the baby to the toothbrushing can be still further lessened to a certain extent.

Further, as the toothbrushing operation is performed or implemented, the bristles 32 which are anchored to the tongue cleaning section 60 which is integrally coupled to the curved portion of the teeth cleaning section of the bristle holder 30, clean the surface of the tongue of the baby, whereby a coating existing on the surface of the tongue of the baby can be effectively removed.

Also, by disassembling the bristle holder 30 and the intermediate engaging member 20 from each other and sterilizing and disinfecting them in boiling water, sanitization can be maintained.

As a result, by the toothbrush according to the present invention, advantages are provided in that, since first through third grooves of a toothbrush body, an intermediate engaging member and a teeth cleaning section of a bristle holder have substantially U-shaped contours, respectively, all of upper teeth or all of lower teeth which are formed in gums of a baby, can be simultaneously cleaned. Also, due to the fact that the bristle holder and a plurality of bristles are made from a soft material such as silicon, awkwardness or uncomfortableness is not induced when they are brought into contact with the teeth and gums of the baby. At this time, the plurality of bristles which are anchored at one ends thereof to a surface of the teeth cleaning section of the bristle holder, define different profiles at posterior teeth and anterior teeth of the baby, in a manner such that they can simultaneously clean buccal, lingual and occlusal surfaces of the posterior teeth and labial and lingual surfaces of the anterior teeth. As a consequence, after the toothbrush of the present invention is received in the mouth of the baby, in a state wherein the plurality of bristles are brought into contact with the teeth and gums of the baby, vibration is generated using a first vibration generating section, whereby, as the toothbrush is continuously moved a little at a time in forward, rearward, leftward or rightward directions, all of upper teeth or all of lower teeth can be simultaneously cleaned. Moreover, because a tongue cleaning section is integrally coupled to a curved portion of the teeth cleaning section of the bristle holder, a coating existing on a surface of the tongue of the baby can be simultaneously removed while the teeth are cleaned.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A toothbrush comprising:

a toothbrush body having a handle and a first vibration generating section and possessing a first groove which has substantially a U-shaped contour;

an intermediate engaging member detachably engaged into the first groove of the toothbrush body, having substantially a U-shaped configuration, and possessing a second groove which has substantially a U-shaped contour;

a bristle holder having anchored thereto a plurality of bristles, the bristle holder including a teeth cleaning section and a tongue cleaning section;

the teeth cleaning section being detachably fitted into the second groove of the intermediate engaging member, having substantially a U-shaped configuration, and possessing a third groove which has substantially a U-shaped contour to receive therein upper or lower teeth of a person; and the tongue cleaning section integrally coupled to a curved portion of the teeth cleaning section for removing a coating existing on a surface of the tongue of the person.

2. The toothbrush as claimed in claim 1, further comprising:

a remote controller including at least one switch for controlling an operation of the first vibration generating section, a speaker for outputting music, a light emitting section capable of flickering, and a second vibration generating section for exerting vibration to an operator's hand, the remote controller being connected to the first vibration generating section of the toothbrush body through a wire.

3. The toothbrush as claimed on claim 2, wherein each of the first through third grooves of the toothbrush body, the intermediate engaging member and the teeth cleaning section of the bristle holder, respectively, has substantially the U-shaped contour in a manner such that it conforms to an outline of gums of the person.

4. The toothbrush as claimed in claim 1, wherein the bristle holder and the plurality of bristles are made from silicon.

5. The toothbrush as claimed in claim 1, wherein the bristles which are anchored at one end thereof to a surface of the teeth cleaning section of the bristle holder, define a variety of different profiles in a manner such that they can simultaneously clean buccal, lingual and occlusal surfaces of posterior teeth and labial and lingual surfaces of anterior teeth of the person.

* * * * *